United States Patent [19]

Dwyer-Hallquist et al.

[11] Patent Number: 4,837,210

[45] Date of Patent: Jun. 6, 1989

[54] FLUORAN DERIVATIVES AND THEIR USE IN RECORDING MATERIALS

[75] Inventors: Patricia Dwyer-Hallquist, Oshkosh; William J. Becker, Appleton; Robert E. Miller, Appleton; Kenneth D. Glanz, Appleton, all of Wis.

[73] Assignee: Appleton Papers Inc., Appleton, Wis.

[21] Appl. No.: 7,252

[22] Filed: Jan. 27, 1987

[51] Int. Cl.[4] .................. C07D 265/30; C07D 405/14; C07D 311/88

[52] U.S. Cl. .................................... 544/150; 544/375; 546/196; 548/525; 549/226

[58] Field of Search ........................ 549/226; 546/196; 544/150, 375; 548/525

[56] References Cited

U.S. PATENT DOCUMENTS

| | | | |
|---|---|---|---|
| 3,959,571 | 5/1976 | Yahagi et al. | 549/226 |
| 4,330,473 | 5/1982 | Hatano et al. | 549/226 |
| 4,442,176 | 4/1984 | Nagaoka et al. | 503/208 |
| 4,444,591 | 4/1984 | Kawai et al. | 549/226 |
| 4,536,220 | 8/1985 | Kondo et al. | 549/226 |
| 4,629,800 | 12/1986 | Yonese et al. | 549/226 |

FOREIGN PATENT DOCUMENTS

| | | | |
|---|---|---|---|
| 34442 | 11/1972 | Japan | 549/226 |

*Primary Examiner*—Richard L. Raymond
*Assistant Examiner*—Mark W. Russell
*Attorney, Agent, or Firm*—Paul S. Phillips, Jr.; Benjamin Mieliulis

[57] ABSTRACT

The invention relates to novel fluoran compounds of the general formula

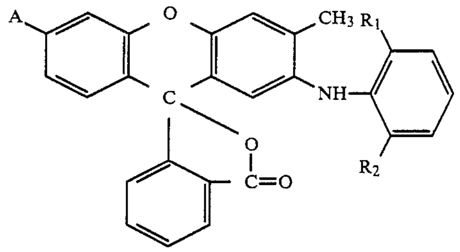

wherein $R_1$ and $R_2$, each independently of the other, are lower alkyl;

A is

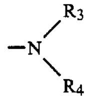

or a pyrrolidinyl, piperidino, morpholino or piperazino radical; and $R_3$ and $R_4$, each independently of the other, are $C_1$–$C_{12}$ alkyl, cycloalkyl, phenyl or phenyl substituted by lower alkyl or lower alkoxy.

These compounds are particularly suitable for use as color formers in pressure-sensitive or heat-sensitive recording materials.

8 Claims, No Drawings

FLUORAN DERIVATIVES AND THEIR USE IN RECORDING MATERIALS

The present invention relates to certain chromogenic fluoran compounds and to the use thereof as color formers in recording materials.

The fluorans have the general formula

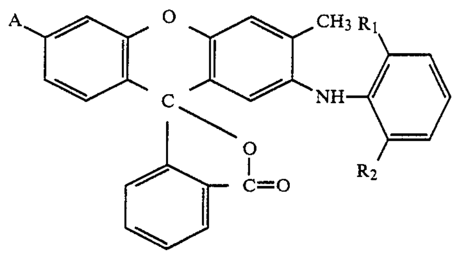

wherein $R_1$ and $R_2$, each independently of the other, are lower alkyl;

A is

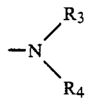

or a pyrrolidinyl, piperidino, morpholino or piperazino radical; and $R_3$ and $R_4$, each independently of the other, are $C_1$-$C_{12}$ alkyl, cycloalkyl, phenyl or phenyl substituted by lower alkyl or lower alkoxy.

In the context of the present invention lower alkyl are those alkyl groups containing one through four carbon atoms, lower alkoxy are those alkoxy groups containing one through four carbon atoms and cycloalkyl are those cycloalkyl groups containing five or six carbon atoms.

Novel chromogenic fluoran compounds have been discovered. These compounds are initially substantially colorless but produce grey black colored products on reaction with certain acidic developer materials. It is an object of this invention to provide such fluoran compounds, methods for making them and mark-forming systems containing them.

It is another object of this invention to provide chromogenic compounds which are resistant to hue shifts of the colored products upon exposure to light.

It is yet another object of this invention to provide chromogenic fluoran compounds which are resistant to discoloration of the uncolored material upon exposure to ambient conditions.

It is still another object of this invention to provide chromogenic fluoran compounds which, when incorporated into recording materials, produce enhanced image density and/or improved background coloration characteristics.

U.S. Pat. No. 4,226,912 discloses a presumed mixture of two or more of the following isomers:

3-diethylamino-6-methyl-7-(2',3'-dimethylanilino)fluoran;

3-diethylamino-6-methyl-7-(2',4'-dimethylanilino)fluoran;

3-diethylamino-6-methyl-7-(2',5'-dimethylanilino)fluoran;

3-diethylamino-6-methyl-7-(2',6'-dimethylanilino)fluoran;

3-diethylamino-6-methyl-7-(3',4'-dimethylanilino)fluoran; and 3-diethylamino-6-methyl-7-(3',5'-dimethylanilino)fluoran.

U.S. Pat. No. 4,330,473 discloses 3-diethylamino-6-methyl-7-(2',4'-dimethylanilino)fluoran;

3-diethylamino-6-methyl-7-(2',4',5'-trimethylanilino)fluoran;

3-diethylamino-6-methyl-7-(2',3',5',6'-tetramethylanilino)fluroan; and 3-diethylamino-6-methyl-7-(2',3',4',5',6'-pentamethylanilino)fluoran.

U.S. Pat. No. 4,442,176 discloses 3-diethylamino-6-methyl-7-(2',3'-dimethylanilino)fluoran;

3-diethylamino-6-methyl-7-(3',4'-dimethylanilino)fluoran; and 3-diethylamino-6-methyl-7-(2',5'-dimethylanilino)fluoran.

U.S. Pat. No. 4,473,832 discloses 3-diethylamino-6-methyl-7-(2',4'-dimethylanilino)fluoran.

U.S. Pat. No. 4,482,905 discloses a presumed mixture of two or more of the following isomers:

3-diethylamino-6-methyl-7-(2',3'-dimethylanilino)fluoran;

3-diethylamino-6-methyl-7-(2',4'-dimethylanilino)fluoran;

3-diethylamino-6-methyl-7-(2',5'-dimethylanilino)fluoran;

3-diethylamino-6-methyl-7-(2',6'-dimethylanilino)fluoran;

3-diethylamino-6-methyl-7-(3',4'-dimethylanilino)fluoran; and 3-diethylamino-6-methyl-7-(3',5'-dimethylanilino)fluoran.

U.S. Pat. No. 4,629,800 discloses

3-N-ethyl-N-butylamino-6-methyl-7-(2',3'-dimethylanilino)fluoran;

3-N-methyl-N-propylamino-6-methyl-7-(2',4'-dimethylanilino)fluoran;

3-N-ethyl-N-butylamino-6-methyl-7-(2',5'-dimethylanilino)fluoran;

3-dibutylamino-6-methyl-7-(2',3'-dimethylanilino)fluoran;

3-dibutylamino-6-methyl-7-(2',4'-dimethylanilino)fluoran;

3-dibutylamino-6-methyl-7-(2',5'-dimethylanilino)fluoran;

3-dipropylamino-6-methyl-7-(2',3'-dimethylanilino)fluoran; and 3-dipropylamino-6-methyl-7-(2',4'-dimethylanilino)fluoran.

Important groups of colorable fluoran compounds of the present invention may be defined by the formula

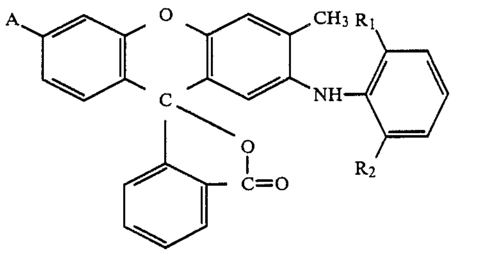

wherein $R_1$ and $R_2$, each independently of the other, are lower alkyl;

A is

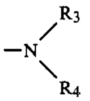

or a pyrrolidinyl, piperidino, morpholino or piperazino radical; and $R_3$ and $R_4$, each independently of the other, are $C_1$–$C_{12}$ alkyl, cycloalkyl, phenyl or phenyl substituted by lower alkyl or lower alkoxy.

Among the more important compounds of this invention are the ones defined by the formula

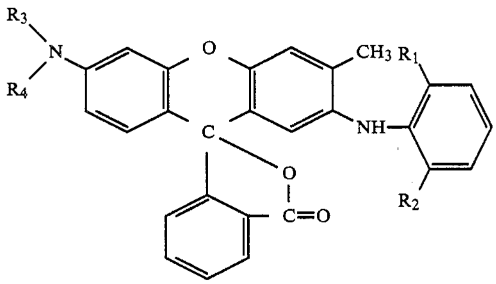

wherein $R_1$ and $R_2$, each independently of the other, are lower alkyl; and $R_3$ and $R_4$, each independently of the other, are $C_1$–$C_{12}$ alkyl, cycloalkyl or phenyl.

The more preferred among the compounds of this invention are the ones represented by the following formula

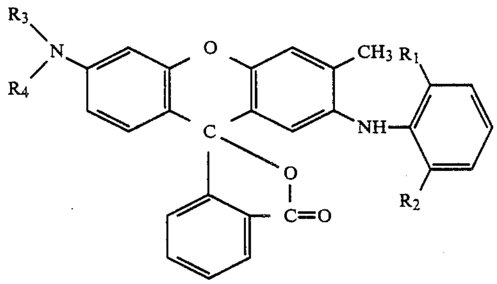

wherein $R_1$ and $R_2$, each independently of the other, are methyl, ethyl or propyl; and $R_3$ and $R_4$, each independently of the other, are $C_1$–$C_8$ alkyl, cycloalkyl or phenyl.

Most preferred among the compounds of this invention are those represented by the formula

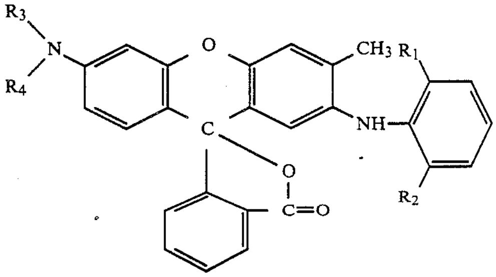

wherein $R_1$ and $R_2$, each independently of the other, are methyl or ethyl; and $R_3$ and $R_4$, each independently of the other, are lower alkyl.

The fluoran compounds of this invention can be synthesized by a process, known in the art, which comprises contacting an anilide of the structure

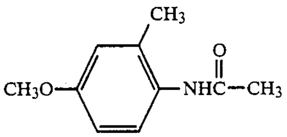

with a compound of the structure

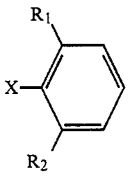

wherein X is halogen, most commonly bromine, and deacetylating the resultant intermediate to produce a diphenylamine of the structure

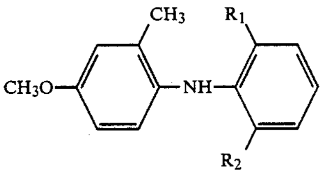

and thereafter condensing said diphenylamine with a compound of the structure

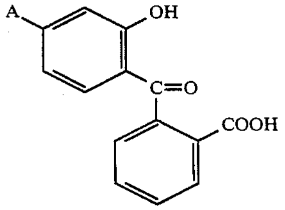

wherein $R_1$, $R_2$ and A have the given meanings.

The fluoran compounds of this invention can also be synthesized by a process, known in the art, which comprises contacting an anilide of the structure

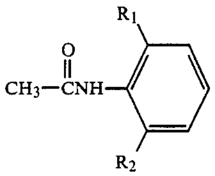

with a compound of the structure

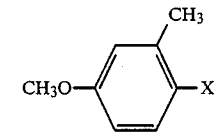

and deacetylating the resultant intermediate to produce a diphenylamine of the structure

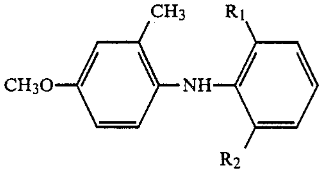

and thereafter condensing said diphenylamine with a compound of the structure

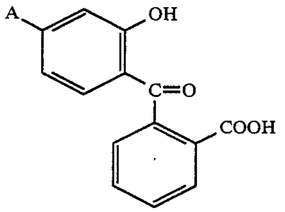

wherein $R_1$, $R_2$, X and A have the given meanings.

The following is provided as a detailed example of the production of a chromogenic fluoran compound of the present invention.

EXAMPLE 1

3-di-n-butylamino-6-methyl-7-(2′,6′-dimethylanilino) fluoran

A mixture of 14.3 g of 3-methoxy-6-acetylaminotoluene, 17.8 g of 2-bromo-m-xylene, 6.6 g of potassium carbonate, and 0.3 g of copper (I) iodide was stirred for 42 hours at 160°–210° C. After the reaction mixture was cooled, 22.9 g of potassium hydroxide and 66 ml of n-amyl alcohol were added to the mixture, which was then refluxed for 3.5 hours. Then the reaction mixture was cooled and washed with hot water. The n-amyl alcohol was removed by distillation, and the remaining reaction mixture was distilled under reduced pressure to obtain 5.5 g (28 percent of theoretical yield) of 3-methoxy-6-(2′,6′-dimethylanilino)toluene.

A mixture of 8.4 g of ortho-(4-di-n-butylamino-2-hydroxybenzoyl)benzoic acid and 23 ml of concentrated sulfuric acid was cooled in an ice bath and to this was added 5.5 g of 3-methoxy-6-(2′,6′-dimethylanilino)toluene. The resulting mixture was stirred for 19.5 hours at room temperature. The mixture was poured into 130 ml of ice water. The precipitate was filtered off, washed with water, and refluxed with 60 ml of toluene and 7.0 g of sodium hydroxide dissolved in 16 ml of water for 1.5 hours. The toluene layer was separated, washed with hot water, dried and filtered. Then the toluene was removed by coevaporation with methanol under reduced pressure. The residue was recrystallized from methanol. The product, 5.6 g (43 percent of theoretical yield) of 3-di-n-butylamino-6-methyl-7-(2′,6′-dimethylanilino)fluoran, was obtained as an off-white powder having a melting point of 170°–172° C. The mass spectrum, H-NMR, and IR of this product were consistent with the named structure.

The chromogenic fluoran compounds of this invention are eligible for use in pressure-sensitive and thermally-sensitive mark-forming systems. Pressure-sensitive mark-forming systems provide a marking system of disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark. In such pressure-sensitive mark-forming systems the chromogenic fluoran compounds of this invention will typically be used in combination with other chromogenic compounds which individually produce marks of different colors so that in combination the reaction between the chromogenic materials and the acidic color developer material produce a mark having a black perceived image. This black mark-forming system constitutes a specific subsidiary feature of the invention.

The pressure-rupturable barrier, which maintains the mark-forming components in isolation, preferably comprises microcapsules containing liquid solvent solution. The microcapsules are coated on a support sheet, preferably along with protective stilt material such as uncooked starch particles as disclosed in U.S. application Ser. No. 806,696, filed Mar. 12, 1969 and now abandoned, and a divisional U.S. application based thereon, Ser. No. 857,348, filed December, 1977 and now abandoned.

The microencapsulation process utilized to make the above-referenced microcapsules can be chosen from the many known in the art. Well known methods are disclosed in U.S. Pat. Nos. 2,800,457; 3,041,29; 3,533,958; 3,755,190; 4,001,140 and 4,100,103. Any of these and other methods are suitable for encapsulating the liquid solvent containing the chromogenic compounds of this invention.

The method of marking comprises providing a chromogenic fluoran compound of the present invention and bringing such chromogenic compound into reactive contact, in areas where marking is desired, with an acidic color developer material to produce a colored form of the chromogenic compound.

The acidic materials can be any compound within the definition of a Lewis acid, i.e. an electron acceptor. These materials include clay substances such as attapulgite, bentonite and montmorillonite and treated clays such as silton clay as disclosed in U.S. Pat. Nos.

3,622,364 and 3,753,761, materials such as silica gel, talc, feldspar, magnesium trisilicate, pyrophyllite, zinc sulfate, zinc sulfide, calcium sulfate, calcium citrate, calcium phosphate, calcium fluoride and barium sulfate, aromatic carboxylic acids such as salicyclic acid, derivatives of aromatic carboxylic acids and metal salts thereof as disclosed in U.S. Pat. No. 4,022,936, acidic polymeric material such as phenol-formaldehyde polymers, phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof as disclosed in U.S. Pat. No. 3,672,935, biphenols as disclosed in U.S. Pat. No. 3,244,550 and addition products of a phenol and a diolefinic alkylated or alkenylated cyclic hydrocarbon as disclosed in U.S. Pat. No. 4,573,063.

Thermally-sensitive mark-forming systems are well known in the art and are described in many patents, for example U.S. Pat. Nos. 3,539,375; 3,674,535; 3,746,675; 4,151,748; 4,181,771 and 4,246,318. In these systems basic chromogenic material and acidic color developer material are contained in a coating on a substrate which, when heated to a suitable temperature, melts or softens to permit said materials to react, thereby producing a colored mark.

The following examples are given to illustrate some of the features of the present invention and should not be considered as limiting. In these examples all parts are by weight and all measurements are in the metric system, unless otherwise stated.

The compounds of this invention and the reference compound listed in Table 1 were subjected to certain tests and/or incorporated into mark-forming record systems as described, infra.

TABLE 1

| Example No. | Fluoran Compound |
|---|---|
| 1 | 3-dibutylamino-6-methyl-7-(2',6'-dimethylanilino)fluoran |
| 2 | 3-dibutylamino-6-methyl-7-(2',6'-diethylanilino)fluoran |
| 3 | 3-diethylamino-6-methyl-7-(2',6'-diethylanilino)fluoran |
| Reference Material 1 | A mixture of two or more of the following isomers possibly present from the method of synthesis: 3-dibutylamino-6-methyl-7-(2',3'-diethylanilino)fluoran; 3-dibutylamino-6-methyl-7-(2',4'-diethylanilino)fluoran; 3-dibutylamino-6-methyl-7-(2',5'-diethylanilino)fluoran; 3-dibutylamino-6-methyl-7-(2',6'-diethylanilino)fluoran; 3-dibutylamino-6-methyl-7-(3',4'-diethylanilino)fluoran; and 3-dibutylamino-6-methyl-7-(3',5'-diethylanilino)fluoran |
| Reference Material 2 | 3-dibutylamino-6-methyl-7-(2',3',5',6'-tetramethylanilino)fluoran |
| Reference Material 3 | 3-dibutylamino-6-methyl-7-(2',4',6'-trimethylanilino)fluoran |
| Reference Material 4 | A mixture of two or more of the following isomers possibly present from the method of synthesis: 3-dibutylamino-6-methyl-7-(2',3'-dimethylanilino)fluoran; 3-dibutylamino-6-methyl-7-(2',4'-dimethylanilino)fluoran; 3-dibutylamino-6-methyl-7-(2',5'-dimethylanilino)fluoran; 3-dibutylamino-6-methyl-7-(2',6'-dimethylaniiino)fluoran; 3-dibutylamino-6-methyl-7-(3',4'-dimethylanilino)fluoran; and 3-dibutylamino-6-methyl-7-(3',5'-dimethylanilino)fluoran |

The color former examples of the invention and the color former reference materials were individually incorporated into solutions with the sovents indicated in Table 2:

TABLE 2

| Material | Parts |
|---|---|
| Color former | 5 |
| $C_{10}$-$C_{13}$ alkylbenzene | 76 |
| sec-butylbiphenyl | 19 |

Each color former solution was microencapsulated by polymerization methods utilizing initial condensates as taught in U.S. Pat. No. 4,100,103.

The resulting microcapsule dispersions were mixed with a corn starch binder and wheat starch particles, the mixture was applied as an 18% solids aqueous dispersion to a paper base using a No. 12 wire-wound coating rod and the coating was dried with hot air, producing a dried coating composition as listed in Table 3. This coated sheet is hereinafter referred to as a CB sheet

TABLE 3

| Material | Parts |
|---|---|
| Microcapsules | 74.1 |
| Corn starch binder | 7.4 |
| Wheat starch particles | 18.5 |

The CB sheets were tested against a sheet coated with a composition comprising acid-treated dioctahedral montmorillonite as an acidic developer material (hereinafter referred to as the CF sheet). Such a developer is disclosed in U.S. Pat. Nos. 3,622,364 and 3,753,761, which are hereby incorporated by reference.

Each CB sheet was coupled, coated side-to-coated side with a CF sheet and each resulting CB-CF pair was imaged in a Typewriter Intensity (TI) test. After the image was allowed to fully develop overnight, the image color properties were measured using the Hunter Tristimulus Colorimeter.

The Hunter Tristimulus Colorimeter is a direct-reading L, a, b instrument. L, a, b is a surface color scale (in which L represents lightness, a represents redness-greenness and b represents yellowness-blueness) and is related to the CIE tristimulus values, X, Y and Z, as follows:

$$L = 10Y^{\frac{1}{2}}$$

$$a = \frac{17.5\,[(X/0.98041) - Y]}{Y^{\frac{1}{2}}}$$

$$b = \frac{7.0\,[Y - (Z/1.18103)]}{Y^{\frac{1}{2}}}$$

The Hunter L, a, b scale was designed to give measurements of color units of approximate visual uniformity throughout the color solid. Thus, "L" measures lightness and varies from 100 for perfect white to zero for black, approximately as the eye would evaluate it. The chromaticity dimensions ("a" and "b") give understandable designations of color as follows:

"a" measures redness when plus, gray when zero and greenness when minus

"b" measures yellowness when plus, gray when zero and blueness when minus

The above-described color scales are described fully in Hunter, R. S. "The Measurement of Appearance", John Wiley & Sons, New York, 1975.

Since the objectives of the present invention include providing a color former which produces a gray (rather than green) image initially and/or which resists the usually-occurring red shift upon light exposure of the image, the "a" chromaticity dimension was used to evaluate the above-described TI images. The following was used to calculate the redness-greenness of the image initially and at various indicated time intervals after room light exposure of the images.

$$\Delta a = a_1 - a_o$$

where $a_1$=image;

$a_o$=unimaged CF sheet (background).

The data listed in Table 5 were obtained:

TABLE 5

| Fluoran Compound | Δa | | | | |
|---|---|---|---|---|---|
| Example No. | Initial | 24 Hr. | 48 Hr. | 72 Hr. | $\Delta a_{72} - \Delta a_{Initital}$ |
| 1 | −0.75 | 2.19 | 3.90 | 4.83 | 5.58 |
| 2 | −2.02 | 0.62 | 1.94 | 2.76 | 4.78 |
| 3 | 1.61 | 3.54 | 4.91 | 5.53 | 3.92 |
| Ref. Mat. 1 | −0.85 | 10.89 | 15.77 | 18.31 | 19.16 |
| Ref. Mat. 2 | −7.25 | −1.04 | 3.51 | 6.69 | 13.94 |
| Ref. Mat. 3 | −5.78 | −2.06 | −0.30 | 0.92 | 6.70 |
| Ref. Mat. 4 | 0.51 | 10.50 | 15.17 | 18.29 | 18.80 |

The value of $\Delta a_{Initial}$ represents the grayness of the initial unexposed image and the value of $\Delta a_{72} - \Delta a_{Initial}$ represents the magnitude of the red shift upon 72 hour room light exposure of the image.

From the above data it is readily apparent that images produced by the fluoran compounds of the present invention are initially nearer to gray and/or upon room light exposure shift less to red than images produced by the reference materials.

To further demonstrate the unexpected properties of the fluoran compounds of the present invention, certain of the fluoran compounds of Table 1 were incorporated into thermally-responsive record material which was subjected to typical imaging tests. Each of the record materials was produced substantially according to the procedures of U.S. Pat. No. 4,586,061, which is hereby incorporated by reference.

In manufacturing the record material, a coating composition was prepared which included a fine dispersion of the components of the color-forming system, polymeric binder material, surface active agents and other additives in an aqueous coating medium.

The coating composition was applied as a coated layer on a paper substrate with a #18 wire-wound coating rod and dried, yielding a coating weight of about 5 to 6 grams per square meter of the composition listed in Table 6.

TABLE 6

| Material | %, dry |
|---|---|
| fluoran compound | 6.3 |
| 2,2-bis(4-hydroxyphenyl)-4-methylpentane | 12.7 |
| acetoacet-o-toluidide | 33.5 |
| zinc stearate | 5.0 |
| behenyl alcohol | 3.9 |
| paraffin wax | 1.3 |
| urea-formaldehyde resin pigment | 7.0 |
| silica | 14.7 |
| polyacrylamide | 0.1 |
| polyvinyl alcohol | 15.5 |

The thermally-sensitive record material sheets were imaged by contacting the coated sheet with a metallic imaging block at the indicated temperature for 5 seconds. The density of each image was measured by means of a reflectance reading using a Macbeth reflectance densitometer. A reading of 0 indicates no discernable image. A value of about 0.9 or greater usually indicates good image development. The densities of the images are presented in Table 7.

TABLE 7

| Fluoran Compound | Reflectance Density of Image Developed at Indicated Fahrenheit Temperature | | | | | | | | | | |
|---|---|---|---|---|---|---|---|---|---|---|---|
| Ex. No. | 300° | 275° | 260° | 245° | 230° | 215° | 200° | 185° | 170° | 155° | 140° |
| 2 | 1.02 | 1.00 | 1.01 | 1.02 | 0.98 | 1.02 | 1.10 | 1.08 | 0.99 | 0.62 | 0.31 |
| Ref. 1 | 0.88 | 0.89 | 0.88 | 0.88 | 0.91 | 0.85 | 1.08 | 1.09 | 1.08 | 0.87 | 0.51 |

The background coloration of the thermally-sensitive record material sheets was determined initially and after aging the sheets for three days and 19 days. The background coloration was measured by means of a reflectance reading using a Bausch & Lomb Opacimeter. A reading of 92 indicates no discernable color and the higher the value the less background coloration. The background data are entered in Table 8.

TABLE 8

| Fluoran Compound | Background Coloration | | |
|---|---|---|---|
| Example No. | Unaged | Aged 3 Days | Aged 19 Days |
| 2 | 85.8 | 86.8 | 86.0 |
| Ref. 1 | 81.1 | 80.1 | 76.0 |

The thermally-responsive record material samples were imaged on a Hifax 700 Group 3 facsimile machine sold by Harris/3M Document Products, 903 Commerce Drive, Oak Brook, Illinois 60521. In this imaging test a standard test sheet was employed. The test sheet has a variety of types and densities of images. After images each of the examples in the Hifax equipment, the reflectance density was measured in four corresponding areas of each test sheet. The density of each image was measured by means of a reflectance reading using a Macbeth Reflectance Densitometer. The densities of the images of each sample are presented in Table 9.

TABLE 9

| Fluoran Compound | Reflectance Density | | | |
|---|---|---|---|---|
| Example No. | Area 1 | Area 2 | Area 3 | Area 4 |
| 2 | 1.33 | 1.39 | 1.32 | 1.32 |
| Ref. 1 | 1.20 | 1.29 | 1.29 | 1.29 |

From the data of Tables 7, 8 and 9, it is readily apparent that thermally-responsive recording materials comprising the fluoran compounds of the present invention produce substantially improved image density and/or background coloration.

The invention being thus described, it will be obvious that the same may be varied in many ways. Such variations are not to be regarded as a departure from the spirit and scope of the invention, and all such modifications are intended to be included with the scope of the following claims.

What is claimed is:

1. A fluoran compound of the formula

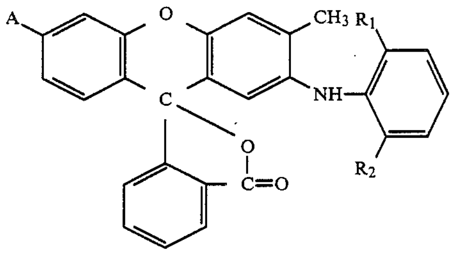

wherein $R_1$ and $R_2$, each independently of the other, are lower alkyl;

A is

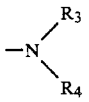

or a pyrrolidinyl, piperidino, morpholino or piperazino radical; and $R_3$ and $R_4$, each independently of the other, are a $C_1$–$C_{12}$ alkyl, cycloalkyl, phenyl or phenyl substituted by a lower alkyl or a lower alkoxy.

2. A fluoran compound according to claim 1 wherein A is

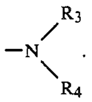

3. A fluoran compound according to claim 2 wherein $R_1$ and $R_2$, each independently of the other, are methyl, ethyl or propyl.

4. A fluoran compound according to claim 3 wherein $R_3$ and $R_4$, each independently of the other, are $C_1$–$C_8$ alkyl, cycloalkyl or phenyl.

5. A fluoran compound according to claim 4 wherein $R_1$ and $R_2$, each independently of the other, are methyl or ethyl; and $R_3$ and $R_4$, each independently of the other, are $C_1$–$C_8$ alkyl.

6. A fluoran compound according to claim 5 wherein $R_3$ and $R_4$, each independently of the other, are lower alkyl.

7. A fluoran compound of the formula

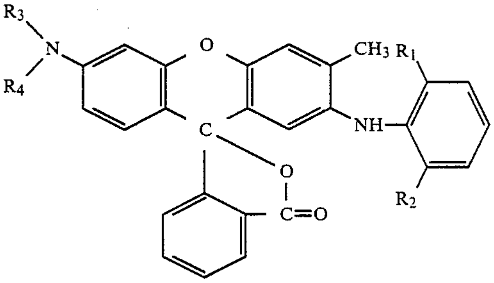

wherein $R_1$ and $R_2$ are methyl or ethyl; and $R_3$ and $R_4$ are a $C_1$–$C_8$ alkyl, cycloalkyl, phenyl or phenyl substituted by a lower alkyl or a lower alkoxy.

8. A fluoran compound according to claim 7 wherein $R_3$ and $R_4$ are $C_1$–$C_8$ alkyl, cycloalkyl or phenyl.

* * * * *